(12) United States Patent
Sorkey et al.

(10) Patent No.: US 8,630,842 B2
(45) Date of Patent: Jan. 14, 2014

(54) COMPUTERIZED SELECTION FOR HEALTHCARE SERVICES

(75) Inventors: Alan J. Sorkey, Shreveport, LA (US); Steven Allen Conrad, Shreveport, LA (US)

(73) Assignee: Zeus Data Solutions, Shreveport, LA (US)

(*) Notice: Subject to any disclaimer, the term of this patent is extended or adjusted under 35 U.S.C. 154(b) by 95 days.

(21) Appl. No.: 12/827,804

(22) Filed: Jun. 30, 2010

(65) Prior Publication Data

US 2012/0004902 A1 Jan. 5, 2012

(51) Int. Cl.
*G06F 17/27* (2006.01)

(52) U.S. Cl.
USPC .............................................. 704/9; 707/101

(58) Field of Classification Search
USPC .................................................................. 704/9
See application file for complete search history.

(56) References Cited

U.S. PATENT DOCUMENTS

| | | | | |
|---|---|---|---|---|
| 6,014,626 A * | 1/2000 | Cohen | | 704/275 |
| 6,347,329 B1 * | 2/2002 | Evans | | 709/202 |
| 6,801,916 B2 * | 10/2004 | Roberge et al. | | 1/1 |
| 7,043,426 B2 * | 5/2006 | Roberge et al. | | 704/231 |
| 7,155,447 B2 * | 12/2006 | Roberge et al. | | 1/1 |
| 7,321,861 B1 * | 1/2008 | Oon | | 705/3 |
| 7,343,565 B2 * | 3/2008 | Ying et al. | | 715/780 |
| 7,379,946 B2 * | 5/2008 | Carus et al. | | 1/1 |
| 7,467,089 B2 * | 12/2008 | Roth et al. | | 704/270 |
| 7,716,040 B2 * | 5/2010 | Koll et al. | | 704/9 |
| 7,716,072 B1 * | 5/2010 | Green et al. | | 705/3 |
| 7,853,446 B2 * | 12/2010 | Allard et al. | | 704/9 |
| 7,904,311 B2 * | 3/2011 | Underwood | | 705/2 |
| 7,908,155 B2 * | 3/2011 | Fuerst et al. | | 705/3 |
| 7,949,542 B2 * | 5/2011 | Hamiter et al. | | 705/2 |
| 8,000,979 B2 * | 8/2011 | Blom | | 705/2 |
| 8,086,471 B2 * | 12/2011 | Gamboa et al. | | 705/2 |
| 2002/0082865 A1 * | 6/2002 | Bianco et al. | | 705/2 |
| 2007/0118384 A1 * | 5/2007 | Gustafson | | 704/275 |
| 2007/0250345 A1 * | 10/2007 | Walker et al. | | 705/2 |
| 2009/0024411 A1 * | 1/2009 | Albro et al. | | 705/2 |
| 2009/0204421 A1 * | 8/2009 | Guimaraes | | 705/2 |
| 2010/0223074 A1 * | 9/2010 | Parker et al. | | 705/3 |
| 2010/0250236 A1 * | 9/2010 | Jagannathan et al. | | 704/9 |
| 2010/0328235 A1 * | 12/2010 | Taute | | 345/173 |
| 2011/0010195 A1 * | 1/2011 | Cohn | | 705/3 |
| 2011/0231207 A1 * | 9/2011 | Easterly | | 705/3 |
| 2011/0301943 A1 * | 12/2011 | Patch | | 704/9 |
| 2011/0306926 A1 * | 12/2011 | Woo | | 604/65 |
| 2012/0004902 A1 * | 1/2012 | Sorkey et al. | | 704/9 |
| 2012/0004932 A1 * | 1/2012 | Sorkey et al. | | 705/3 |

* cited by examiner

*Primary Examiner* — David R Hudspeth
*Assistant Examiner* — Timothy Nguyen
(74) *Attorney, Agent, or Firm* — Fish & Richardson P.C.

(57) ABSTRACT

A method for producing healthcare data records from graphical inputs by computer users. Includes generating a plurality of user input categories, displaying on a graphical display icons that correspond to a first of the user input categories and receiving a first user selection of a first icon of the plurality of icons, and displaying on the graphical display a plurality of icons that correspond to a second of the user input categories and receiving a second user selection of a second icon of the plurality of icons. The method also includes displaying icons that correspond to a physical target on which the medical action or observation is performed and receiving a third user selection of the physical target, and applying a syntax to populate a data record of the action using the at least two of the first, second, and third user selections.

20 Claims, 9 Drawing Sheets

Administered [value:modifier "of"] [modifier] to [base] to treat [value:descriptor] [descriptor]

Modifier = [laceration, fracture, sick]
    Value:laceration = inches; 0-1, 1-2, 2-3, 3-4, 4-5, 5-6
    Value:fracture = simple, compound, greenstick, transverse, oblique, comminuted
    .
    .
    .
    .

COMPUTERIZED SELECTION FOR HEALTHCARE SERVICES

TECHNICAL FIELD

This document relates to mechanisms by which computer users can interact with a computer system to record information about patients in a healthcare system.

BACKGROUND

Healthcare professionals must do much more than care for patients in order to provide patient care. They also need to be part-time administrators, charting the care that has been provided so as to create a complete patient record so that they and other providers may know what treatments the patient has received, and to know which drugs the patient is taking (to prevent harmful drug interactions), for example. They also need to enter information needed for billing purposes, so that their employer can be reimbursed for the care they provide. Sometimes, physicians may spent large portions of their day writing in charts and the like, or may employ transcription services to convert their voice recordings into relevant textual information, and then employ other staff to get that information connected to the appropriate records. Each such step adds expense and the chance for errors to the process. Also, paper record keeping suffers from limited or lack of access, illegibility, incompleteness, need for storage, and a lack of safety safeguards.

Electronic records, including electronic medical records (EMRs), electronic health records (EHRs), and electronic billing, have simplified the recordkeeping task and made it more powerful. For example, EMRs can be searched electronically to identify patients in need of certain types of care. EMRs may also be analyzed electronically to identify problems with a patient that may not have been apparent to the team caring for the patient. Also, EMRs allow voluminous data to be stored and accessed for a patient, and for the data to be accessed from any location and my multiple different parties at the same time. Many EMR systems, however, simply attempt to emulate the traditional paper chart. by providing users with templates that are populated with selection boxes, drop-down boxes and text boxes for the entry of findings. Such approaches may require numerous time-consuming mouse clicks or screen touches, diminished operator efficiency and operator fatigue.

SUMMARY

This document describes systems and techniques that may be used for electronically recording notes and other data regarding care that has been provided to a patient in a healthcare setting. The systems and techniques may be used to allow a caregiver to enter information with a minimized number of mouse-clicks, selections and other operations.

For example, a simplified, contextual graphical user interface (GUI) may be provided to a healthcare provider in the form of a plurality of zones, where each zone includes an iconic representation of a healthcare-related object. One zone may include subjects, in the grammatical sense, and another modifiers, while a third zone displays portions of a human body. A healthcare provider may select, e.g., on a touch screen interface, the subject and modifier and may select a part of the body on which the particular action was performed. As one example, the subject may be an icon that identifies the type of caregiver that performed the action (e.g., resident physician, or nurse), the modifier may be the action performed (e.g., vital sign readings, IV administration, etc.), and the part of the body may be where the action occurred, if appropriate, such as a compression bandage to the patient's left arm. The system may then use a predefined syntax to convert the icon selections to a data representation of the particular activity.

In one implementation, a computer-implemented method for producing healthcare data records from graphical inputs by computer users is disclosed. The method comprises generating a plurality of user input categories, and (a) displaying on a graphical display a plurality of icons that correspond to a first of the user input categories, and receiving a first user selection of a first icon of the plurality of icons; (b) displaying on the graphical display a plurality of icons that correspond to a second of the user input categories, and receiving a second user selection of a second icon of the plurality of icons; and (c) displaying on the graphical display one or more icons that correspond to a physical target on which a medical action or observation is performed, and receiving a third user selection of a physical target. The method also comprises applying a syntax to populate a data record of the medical action or observation using the at least two of the first, second, and third user selections.

In some aspects, at least two of the first, second, and third user selections are made by a dragging motion of a user dragging their finger or a stylus continuously across a touch screen display on which the icons are shown until all selections are made. The dragging motion can move in a single direction through the first icon, the second icon, and the physical target. The method can also comprise cancelling an input operation if the user releases contact with the touch screen display before making all three selections. Also, the physical target can be selected before the second icon is selected, and the second icon can be selected before the first icon is selected, so that a user specifies a physical target for an action before specifying the action.

In certain other aspects, the method further comprises, after receiving the selection of the first icon, changing icons displayed in the second of the user input categories, to provide icons that correspond to the selected icon. The changed icons can include icons of modifiers for a medical procedure or observation selected with the first icon. Also, applying a syntax to populate a data record of the action using the at least two of the first, second, and third user selections can include (a) identifying at least an object and an action that correspond to the user inputs; and (b) constructing a sentence from a template or tree, and adding the object and the action to the template. Moreover, applying a syntax to populate a data record of the action using the at least two of the first, second, and third user selections can comprise (a) identifying at least two objects and an action that correspond to the user inputs; and (b) constructing a sentence using a syntactical structure by adding the at least two objects as a grammatical subject and object of the sentence, and the action as a grammatical verb form of the sentence.

In certain other aspects, the method further comprises identifying a patient who corresponds to the user selections, and adding a natural language sentence generated using the syntax.

In another implementation, a computer-implemented system for producing healthcare data records from graphical inputs by caregivers is disclosed. The system includes a display controller to generate data for displaying graphical icons in a plurality of categories, wherein the categories represent a physical target in association with which a medical action is performed, an object that corresponds to a healthcare treatment or action, and a modifier that represents a modification of the object that corresponds to a health care treatment or action; an input processor to receive user selections of graphical icons on a graphical display; and a description builder programmed to apply syntactical rules based on the selected graphical icons to produce a prose of a description for a medical action represented by the selected graphical icons. The display controller can be programmed to change icons displayed in a second group of displayed icons, in response to a user selection of an icon in a first group of icons.

In certain aspects, the display controller is programmed to arrange the groups of icons visually in three rows or columns, with the physical target in one end row or column, the object that corresponds to a healthcare treatment in the other end row or column, and the modifier in the middle row or column. The input processor can be programmed to identify a continuous dragging motion across a touch screen display on which the icons are shown, without releasing contact with the touch screen until all selections are made. Also, the description builder can be programmed to reference a plurality of syntactical rules and to add terms to a sentence based on the user-selected icons. For its part, the display controller can be programmed to change a second group of displayed icons, in one or more columns or rows, in response to a user selection in a first group of displayed icons.

The system can also include an electronic medical record interface to receive the prose for the description, to identify a patient who corresponds to the healthcare treatment or action, and to add the prose description to an electronic medical record for the identified patient. The interface can be programmed to store the prose description as a sentence in which: (a) the object that corresponds to the healthcare treatment or action is expressed as a grammatical subject; (b) the physical target is expressed as a grammatical object; and (c) the modifier is expressed as a grammatical modifier. Also, the interface can be programmed to store a syntactical description of the healthcare treatment or action.

In yet another implementation, a computer-implemented system for producing healthcare data records from graphical inputs by caregivers is disclosed. The system comprises a display controller to generate data for displaying graphical icons in a plurality of categories, wherein the categories represent a body part on which an medical action is performed or observed, an object that corresponds to a healthcare treatment or observation, and a modifier that represents a modification of the object that corresponds to a health care treatment or observation, and an input processor to receive user selections of graphical icons on a graphical display. The system also comprises means for building a prose description of a medical action represented by the selected graphical icons.

The details of one or more embodiments are set forth in the accompanying drawings and the description below. Other features and advantages will be apparent from the description and drawings, and from the claims.

DETAILED DESCRIPTION

This document describes mechanisms by which an operating system may manage interactions with graphical objects that can be viewed by and/or manipulated by a user of a computing device. The mechanisms may display graphical icons for parts of speech that are directed specifically at operations that may be performed by caregivers in a healthcare setting. User may then simply drag across the icons that pertain to actions they have taken for a patient (e.g., treatments performed on the patient, documentation of observations made of the patient, and the like), and a system may arrange the ideas represented by the selected icons into a phrase or sentence that may be added to an electronic medical record and/or a billing record. Such automatic generation of textual or non-textual (e.g., images) content may permit a caregiver to readily move from one patient to another, and not have to spend extensive time each day translating caregiving actions into records. Also, the caregiver may, when recording is convenient, record the actions close in time to when the actions were performed, thus increasing the accuracy of the records.

Figure 1A:
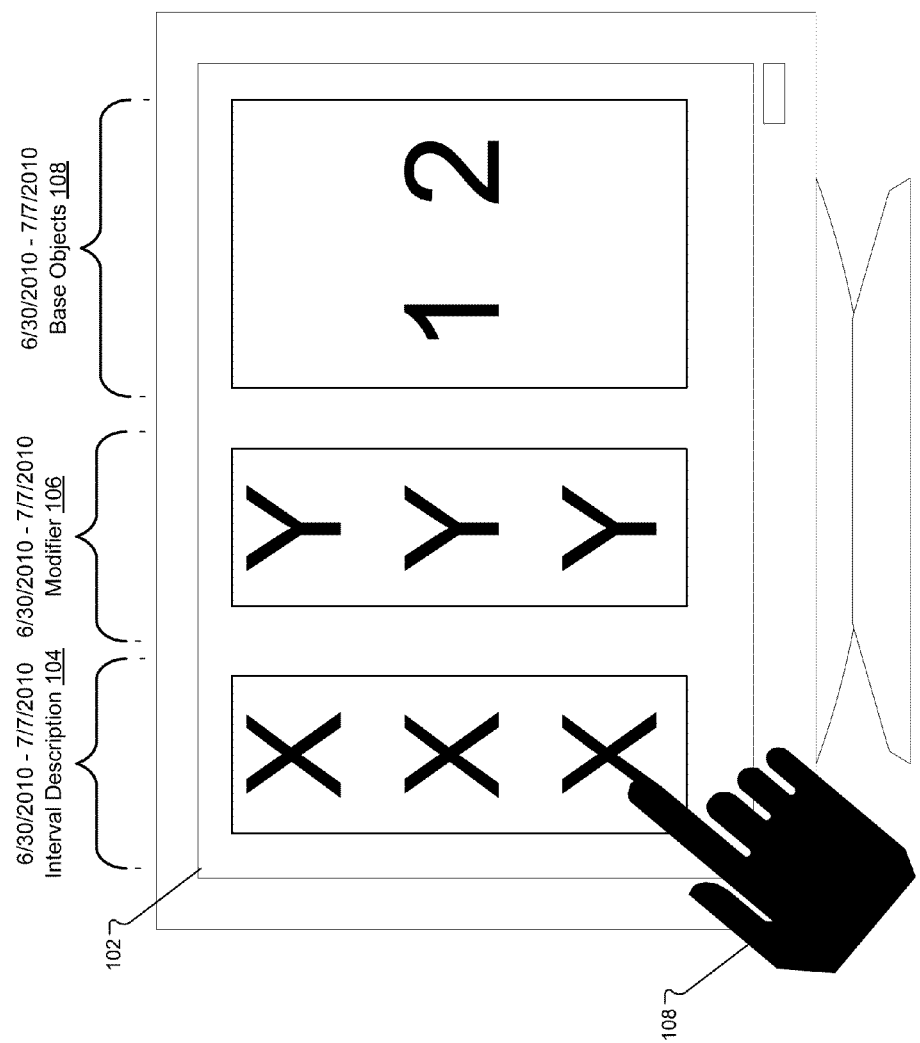
FIG. 1A shows a schematic view of user interaction with a healthcare information input touch screen application.

FIG. 1A shows a schematic view of user interaction with a healthcare information input touch screen application. The figure is intended to show, in broad terms, on-screen graphical elements that may be presented to a caregiver who is seeking to record, to a computer system, information about a caregiving incident.

Om this example, a display 102 is broken spatially into three columns, each of which displays multiple selectable graphical representations, or icons, which are indicated by letters or numbers. A user may select an icon from each column successively to complete a description of an action the user has performed on a patient. Such selection may occur, for example, by the user dragging his or her finger from one side of the display to the other, picking up relevant icons as the user moves.

In this example, the columns are ordered by categories, so that each of the icons in a particular column matches the relevant category. The first column 104 shows descriptions of objects that may be relevant to patient care. Such objects may take a variety of forms, such as instruments used to provide care, problems with the patient as determined by a diagnosis, the type of caregiver, and other such object categories.

The second column 106 includes icons for modifiers that are applicable to the first column. Such modifiers may be used to make more specific the general information from the first column 104. For example, if the first column shows icons of medical instruments, the second column may show actions that can be performed with the instruments. Thus a user may first select an instrument that he or she used on a patient (e.g., an adhesive bandage) and may then select an action that he or she performed with the instrument.

The third column 108 shows "base objects," which define where the action was performed. In this example, there are two icons for the base objects, and they may show an image of a man and a woman. A user may then drag from the second column 106 to a location on an image in the third column 108, where the images in the third column may 108 be mapped so that the location on the images that a user selects (e.g., by dragging over from the second column 106, and then releasing to "drop" their description on a particular body part) can be determined and used for later processing.

This process of a user dragging across columns of icons may be used to automatically generated a description in a textual form. In particular, the first column 104 may provide an object or other noun for a sentence, and the modifier may provide a verb, adjective, or adverb for the sentence, and the final selection may provide a subject for the sentence.

The particular arrangement of icon columns may have associated with it a syntax for a particular sentence, where spaces are left to fill in values for the particular items that a user selects. Thus, in the example here, the sentence may map the sorts of objects and modifiers to be shown on the display 102, and the particular values for the icons that the user chooses may be inserted into the sentence. The final sentence may then be a textual equivalent of the graphical thought that the user entered by selecting the particular icons.

The particular sentence structure may be constructed in various manners. For example, the selections by a user may be matched to one or more input templates, in which portions of a sentence are provided statically in the template, and terms that match the user selections are dynamically inserted into the template. Alternatively, or in addition, a tree structure may be used to construct prose from user graphical selections. The tree may be arranged in a variety of known manners, and may implement an appropriate syntax that includes adequate flexibility to permit simplified gesture inputs by a caregiver for a variety of topics.

Figure 1B:
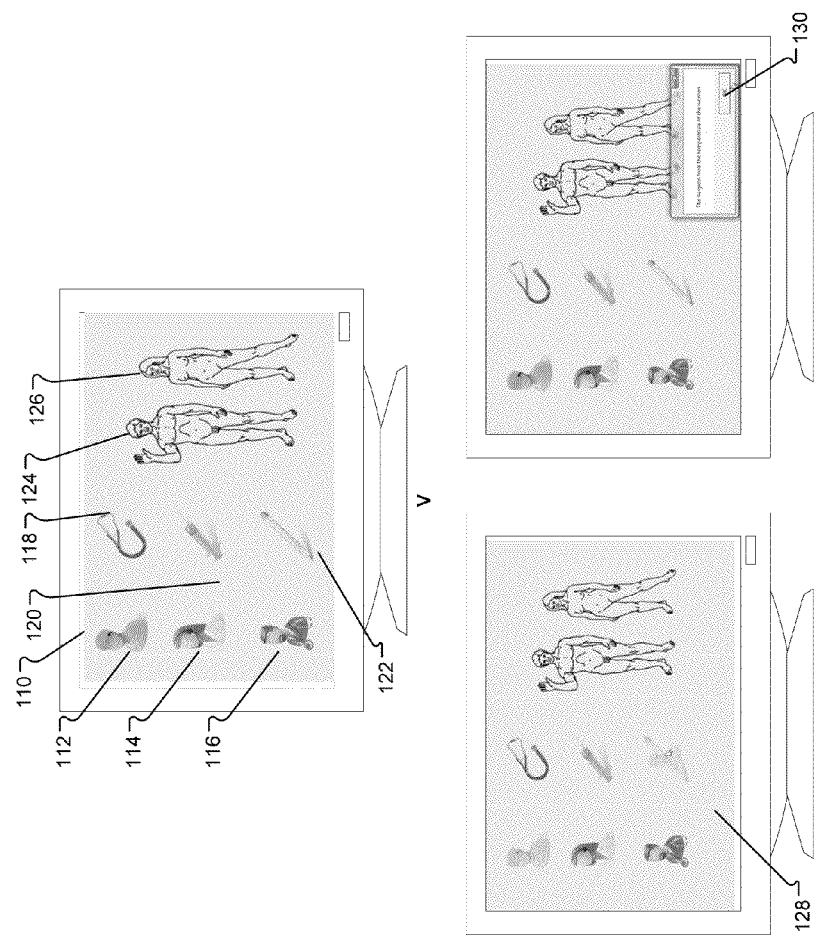
FIG. 1B shows example screen shots for a healthcare information input touch screen application.

FIG. 1B shows example screen shots for a healthcare information input touch screen application. This example has the same form as FIG. 1A, but shows actual data and icons that may be selected by a user. In this example, the first column 110 represents a caregiver type, and the icons show a surgeon 112, a nurse 114, and an attending physician 116. A user may initially touch the display 128 over the icon that represents their role in an organization.

The second column represents an action that may have been taken on a patient by the caregiver. In this example, the column shows stethoscope 118, syringe 120, and thermometer 122 icons. A user may thus, after selecting their appropriate role, slide their finger across the screen to the right and select the syringe. The syringe icon may be associated, in an ontology for generating a description, with the action of "injection." Likewise, the user may select a thermometer, which may be associated with the term "took the temperature." The user may then continue dragging his or her finger to the third column. As the user drags, the selected icons may be "picked up" by his or her finger so that they appear to move with the finger, such as in a shadowed form, at least momentarily. Also, the relevant icons can be made to disappear from their prior locations as an additional feedback mechanism for the user to indicate that the icons have been successfully selected. Such a situation is shown in the second screen 128.

In a last screen, a description box 130 is shown as appearing on the screen. The user, in the meantime, may have dragged his or her finger to the third column until it reached the icon of the woman, and then may have released the finger from the surface of the touch screen. In this simple example, then, the description box 130 provides the sentence "The surgeon took the temperature of the woman."

In this manner, the user interface may provide a simplified approach by which caregivers can enter information into a computer system to reflect actions they performed on patients, and to have those actions converted to a traditional textual form that can be read on a patient record by other caregivers, and can be processed by various automated systems such as billing systems.

Figure 1C:
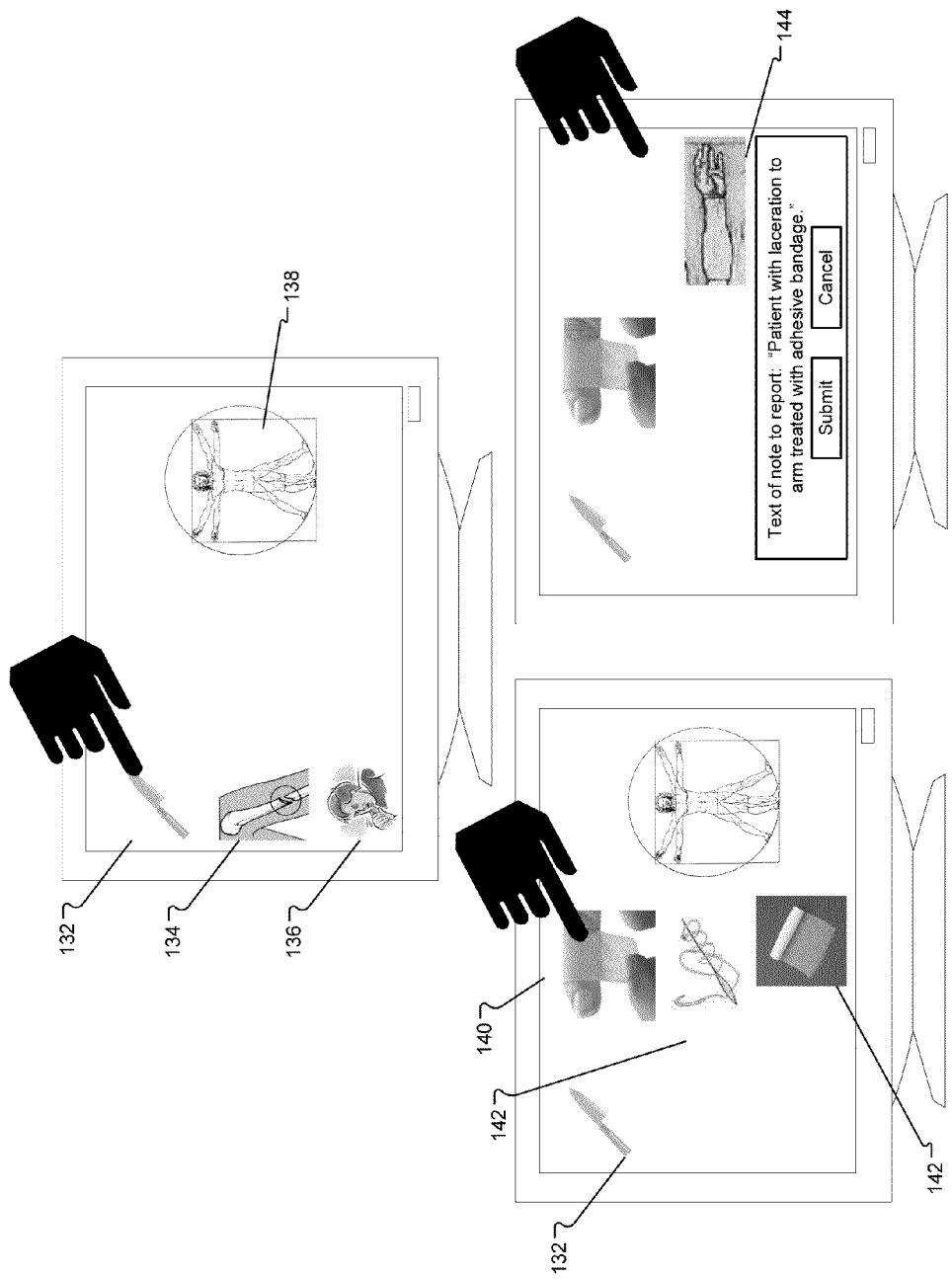
FIG. 1C shows example screen shots for a contextual input application.

FIG. 1C shows example screen shots for a contextual input application. The operations in this figure are similar to those in FIG. 1B, but the icons that appear are generated according to a context of already-selected information from the user. Again, the example is shown in a series of three screen shots that move along progressively in time.

On the first screen, a first column and a third column are initially shown. The third column takes a familiar form of a human body onto which various actions may be dragged to indicate a location where the actions were performed. The first column shows objects in the form of ailments for an incoming patient. In this example, the computer application is being run in a critical care or emergency room area so that common ailments for such an area are shown. The identification of the area in which the application is being run may be made, for example, by the location of the computer, by the identity of the caregiver who has logged onto the computer (e.g., using a password, an ID card, or biometric technology such as a fingerprint swipe).

Additional ailments may be provided for off the screen. In such an example, the user may "scroll" through the other options by swiping his or her finger vertically on the touch screen display, until the relevant ailment appears. In such a situation, the ailments may be sorted from most common to least common, so that the caregiver can find the appropriate icon quickly.

In this example, three ailments are shown. Once, represented by a knife icon 132, covers lacerations to patients who arrive in the critical care center. The second, represented by an icon 134 of a broken arm, represents fractures, which are another common critical care or emergency occurrence. The third, represented by an icon 136 of a person coughing, represents sick patients.

In this example, the user selects the icon 132 to indicate that they treated a patent who had a laceration. Such a selection, by the user pressing on the icon and then moving to the right (a simple press would not indicate a user selection because the user may be starting a scrolling input), causes two changes to the display in this example. First the icons for the other ailments disappear, thus providing an indication that their selection of the laceration icon has been accepted. The user could move back to the left to "undo" the selection, however, and to have the screen return to its original state from the first screen shot.

Second, a middle column of icons has appeared. The column shows icons for actions that modify the selection made in the first column. This middle column was not shown initially because there would have been too many modifiers to cover all of the possible first-column selections. However, once a particular icon is selected in the first column, a smaller number of context-sensitive icons may be generated for the second column. In this example, the generated second column includes an adhesive bandage icon 140, a stitching icon 142, and a gauze bandage icon 142.

Though not shown, other parameters may be display to a user depending on the particular icon he or she chooses. For example, if the user selects the stitches icon, to indicate that they needed to stitch up the initially-selected laceration, the user may be asked to input the number of stitches that were required (e.g., when reimbursement levels are tied to the number of stitches).

In this example, the user selects the adhesive bandage by sliding their finger laterally across it form the location in the first column, on their way to the third column (though they could also tap and pick up their finger for each column). The user has then selected the left arm on the image of the human in the third column to indicate that the stitches were applied to the patient's arm. In response, the icon 138 of the human in the first and second displays has been replaced by a zoomed-in icon 144 of the patient's left arm.

In the final screen shot, the caregiver is also presented with a pop-up box that shows the phrase into which his or her inputs have been translated. In this example, the phrase is "Patient with laceration to arm treat with adhesive bandage." The caregiver is also presented with two selectable controls in the box, so that they can cancel their data entry, e.g., if the sentence is not descriptive of the actions they performed on the patient. They may also choose to submit the description, which may cause the description to be added to the patient's electronic medical record.

A caregiver may be enabled to edit an entry in various manners. For example, a "cancel" or "delete" virtual key may be displayed on a screen, and selection of the button or key may negate the most recently-provided entry. A quick back-and-forth, z-shaped motion with the user's finger, like the motion of a blackboard eraser, may also cause the most recent entry to be negated. Also, a user, after dragging across a full screen of entries and modifiers, may lift their finger and then tap on a desired icon in any row where the caregiver wishes to make a correction. As one example, a physician may miss a desired modifier in a middle column, may nonetheless complete the input motion, and may then go back and tap the correct size, and the generated prose will be modified automatically to match the newly-selected parameter.

Figure 2A:
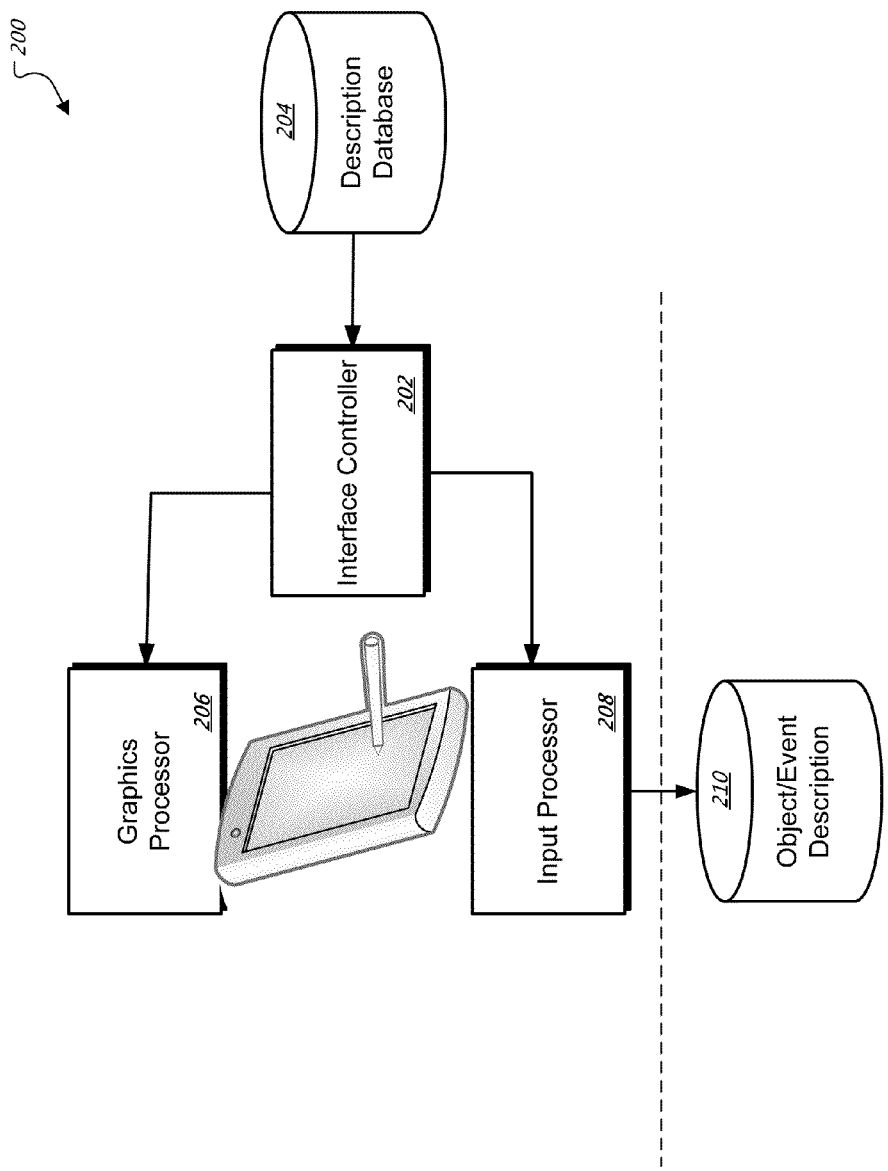
FIG. 2A is a block diagram of a system for providing interaction with a user input.

FIG. 2A is a block diagram of a system for providing interaction with a user input. This is a relatively simple diagram that shows major components of a system for converting user inputs on a graphical interface into textual outputs that describe actions performed on a patient.

A standard touch screen device is shown at the middle of the figure, and is surrounded by components that may be executed on the device, on a separate device such as a server, or a combination of the two. A graphics processor 206 is shown serving the device, and may be a combination of software and hardware components that are programmed to generate displays like those shown in FIGS. 1B and 1C. The graphics processor in particular may select icons to be associated with particular categories relating to patient care, and may arrange the icons in an appropriate manner, grouped in the categories, so that a user may be presented with an intuitive mechanism by which to select particular icons to describe their actions.

An input processor 208 is responsible for receiving information about where selections on a display have been made (e.g., via a touchpad or touch screen), and to coordinate the locations of the selections with information that is currently shown on the display. Thus, for example, the input processor may determine whether a user selected a particular icon, and may provide such information to other components of the system 200.

The graphics processor 206 and input processor 208 may be part of, or otherwise managed by, an interface controller 202. The interface controller 202 accepts information about icons or other graphical elements to be displayed, which may be stored in the description database 204. It may also accept other information, such as the categories within which each element belong, the display coordinates for an element, the relative display position of an element in a category (which may be based on the frequency with which the element is selected in a particular context or environment) and object/event descriptor terms that are associated with each element.

An object/event description may be generated by the system as an output from a user selecting particular elements (via icons) on a display of the device. The object/event description may be simply a textual, prose conversion of the graphical concepts that a caregiver selected on the screen, like the textual descriptions shown in FIGS. 1B and 1C. Other forms of the textual description may also be provided, and they need not take the form of a full, or grammatical, sentence.

Figure 2B:
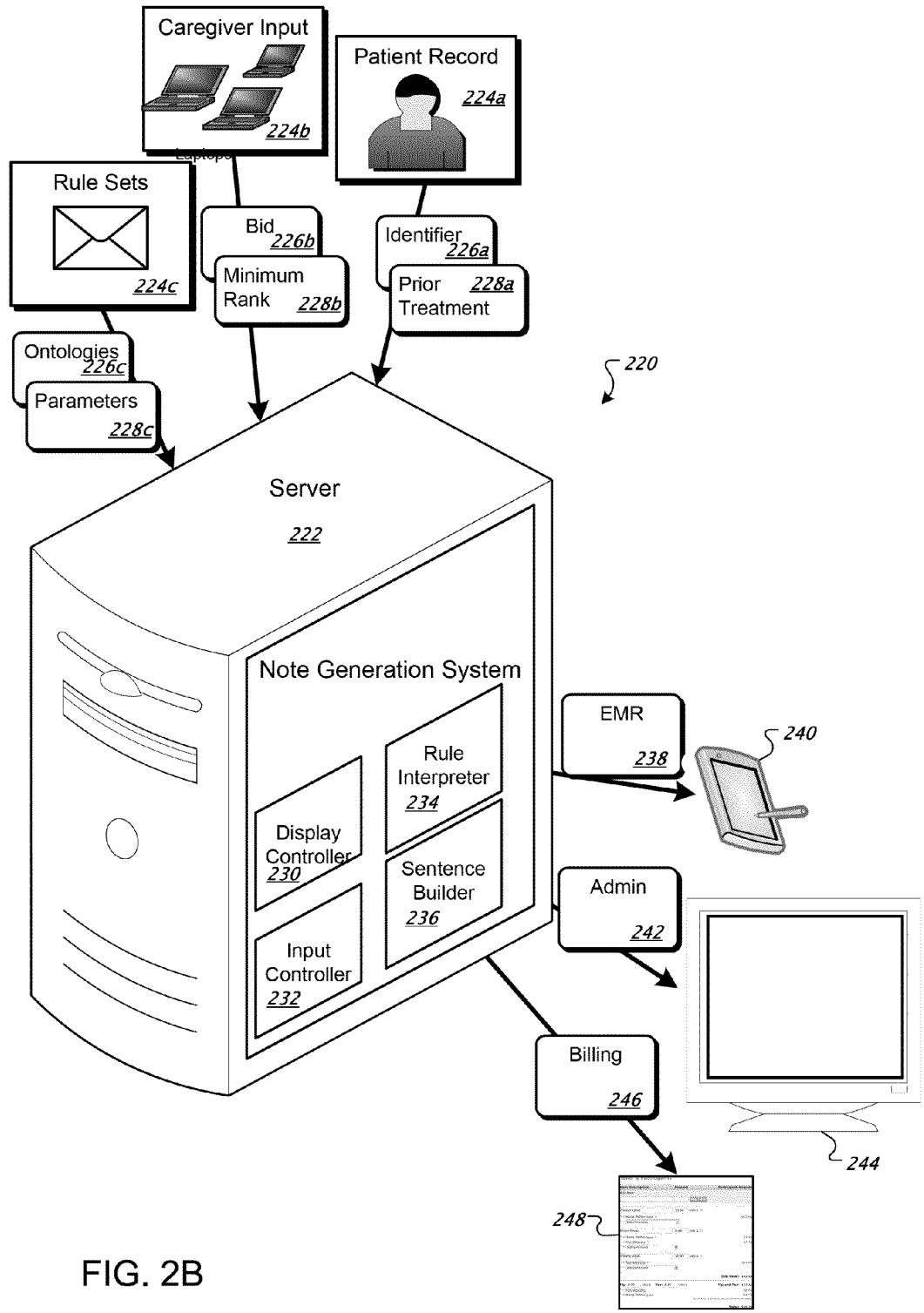
FIG. 2B is a block diagram of a system for generating healthcare notes from caregiver inputs.

FIG. 2B is a block diagram of a system 220 for generating healthcare notes from caregiver inputs. In general, the system 220 responds to graphical inputs from a user, such as the dragging of a user's finger or other form of pointer (e.g., a stylus) such as dragging across icons groups that represent medical objects (e.g., body parts of a patient, or medical instruments) or medical actions or conditions to be performed on the objects, or observed from the objects.

The system 220 in this example centers around server system 222, which may be implemented as one or more computer servers that interact, over a network, such as a LAN or WAN, and/or the internet, with client devices which users of the system 220 employ. The server provides simplified interaction for such users, and translation of user inputs into other forms (e.g., from graphical dragging to a textual description with or without images or other content and meta data). Various structural components within a note generation system of the server system 222 permit such interaction. For example, a display controller 230 may be responsible for providing data used to generate a graphical display of information for a user who is employing the system 220. Such as display may be similar to the displays depicted in FIGS. 1A to 1C. The display controller may access a variety of information sources, including patient records 224a, graphical resources such as libraries of icons, rules and instructions for selecting particular icons, and other such data sources.

An input controller 232 may operate in cooperation with the display controller 230 in order to interpret user input to the system. The input controller may interpret user inputs, including by coordinating inputs at a certain location on a display screen, with information that is displayed on the screen. Thus, for example, the input controller 232 may determine when a pointer that is in contact with a touch screen is over a particular icon or group of icons, and may take programmed actions in response to such determinations.

The particular components discussed here are shown for convenience as being located on the server system 222, though the components may also be located wholly or partly on a client device. For example, using asynchronous JavaScript and XML techniques, a client device may track user interaction with a document and may report to a server system such as server system 222 when a user takes relevant action with respect to the document. The server system 222 may then process such input and may respond asynchronously with information that the client may need. As one example, the server system 222 may provide to a client device mark-up code and other code such as JavaScript code that is integrated with the mark-up code, so as to generate a display like that in FIG. 1B. The code may track a user's sliding of their finger across the various groups of icons, and may wait until the user has identified a relevant number of the icons, before sending such information back to the server 222. At that point, the identification of the icons selected by the user may be transmitted, and the server system 222 may then be responsible for interpreting the user input, for storing information in a central repository about it (e.g., by updating a medical record) and by providing feedback to the physician (e.g., showing a draft addition to the patent medical record, or otherwise confirming that the user's input has been processed).

A rule interpreter 234 and sentence builder 236 operate together to turn user input that occurred in a graphical manner into a form that can more easily be stored and referenced later by the user who entered the data or by other users. The rule interpreter 234 receives a variety of rule sets 224a, which may define ontologies 226c and other parameters 228c. For example, a rule set 224c may define that, when a certain medical device is selected, only certain actions may be identified for that device, so that a user employing the interface of FIG. 1B would be limited in his or her subsequent choices once he or she selected a particular medical device. Such relationships may be defined by one or more ontologies 226c, which defines a representation or model of the relationship between various graphical components that a user selects in a graphical system, and certain words or phrases that may be represented by such selections. Thus, the rule interpreter 234 breaks apart the particular selections made by a user, and the sentence builder puts them together to form a natural language description of the observation or other action that a user enters into a system. Such description may in turn be added to the patent's electronic medical record 238 or accessed from other points.

Various inputs are used by the system 220 to generate graphical displays for interacting with a user and for translating the user's interaction with such displays into other forms of input that can be stored and referenced by other portions of the system 220. As mentioned, for example, rule sets 246c may be provided to the system 220 and can define how user input is translated. Such rules may be provided by a third-party or can be programmed by the users themselves (e.g., by tracing paths through icons and then providing structured outputs that are to correspond to such paths).

Caregiver inputs 224b may also be received, such as via input controller 232. The inputs 224b may take a variety of forms. For example, a user may provide an identifier 226b both for themselves and a patient. User identification may occur via a badge the user wears or via one or more biometric checks (e.g., fingerprint, hand or eye scan, etc.). Patient identification may occur simply by the terminal a user is employing (e.g., the system knows that a terminal is adjacent patient X's bed), by the user typing in information to identify the patient, or by other such mechanisms.

The various inputs that a user may provide may, in appropriate circumstances, include dragging inputs like those discussed with respect to the figures above. As also mentioned, patient record data 224a, such as EMR data, may also be provided to the system 220. Such information may be used to identify the patient 226a, to obtain a gender for the patient, and to identify problems that the patient is facing and treatments the patient is being given 228a, among other things.

The server system 222 may also provide a wide variety of outputs, including outputs that may be used by the users discussed so far, outputs that may be used by other users, and outputs to other sub-systems that are part of a much larger overall healthcare system. For example, various outputs may be provided so as to affect patient EMRs 238, and that can later be viewed on various devices such as laptop, palmtop, netbook, or smartphone computing devices 240. the EMR information may include textual and graphical representations of actions that a user took with respect to a patient, or observations the physician made of the patient. Such observations may be accompanied, for example, by one or more digital images that the user may have taken of the patient. For example, the physician may take a photograph of an injury, such as a laceration to better document in the patient's EMR, the nature and severity of the laceration.

In addition, information may be provided to various administrators 242, such as for review on desktop personal computers 244. For example, administrators may want to "roll up" the information on various procedures and observations made in a system, such as by looking to particular billing codes entered by or on behalf of physicians or nurses. As one example, an administrator may want to identify the rate with which certain procedures are run and compare that rate to comparable other healthcare organizations. Various other uses of such data that is typical of healthcare administrators may also be provided.

Billing information 246 may also be generated by a system that employs server system 222, and may result in a bill 248 being sent to a payer, such as a patient and/or an insurer or managed care program. The billing outputs may, for example, result from a physician tracing a path through groups of icons for objects, actions, and body parts, and thus the occurrence of an associated procedure being registered as having been performed on the relevant patient.

Using these components, the system 220 may provide for simplified input of certain healthcare-related computer interactions. For example, a caregiver may drag cross-wise, wholly from left to right (or downward from top to bottom) across columns of icons, with the icons of a downstream column being affect by what icon was selected in the first column. Such icon selected may be interpreted, in combination, to produce a textual natural language description of the activity that was recorded, perhaps with one or more images or other items being also provided, such as to an EMR.

Figure 3A:
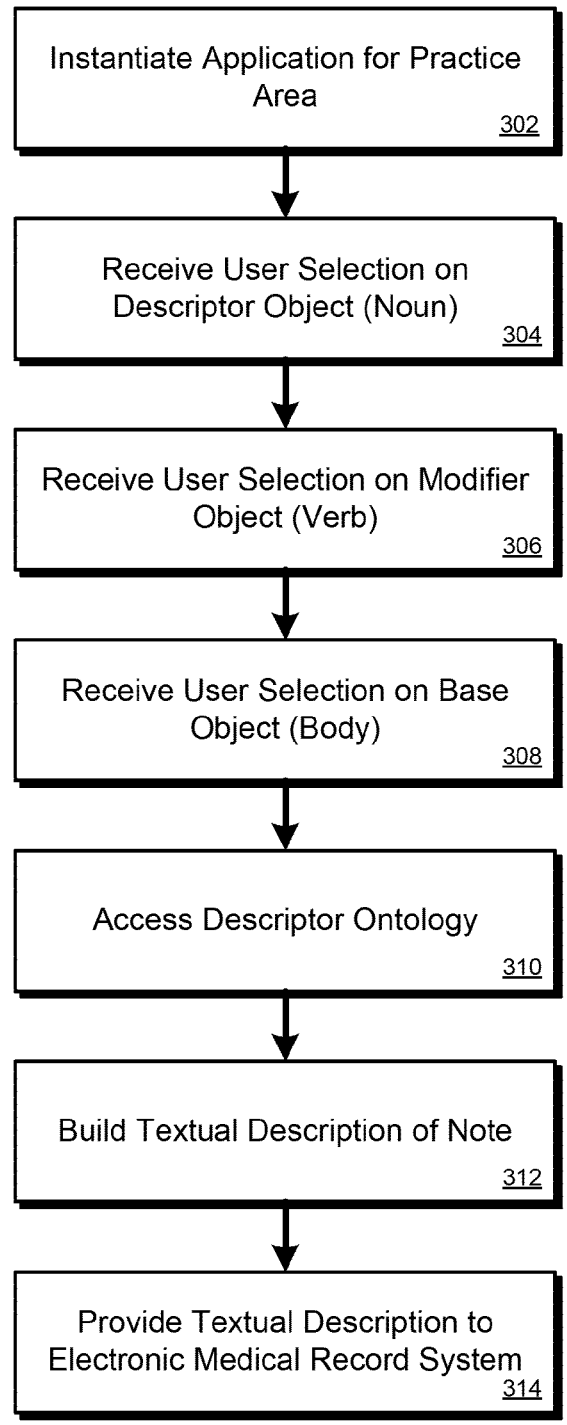
FIGS. 3A and 3B are flow charts of processes for generating healthcare notes from caregiver inputs.
Figure 3B:
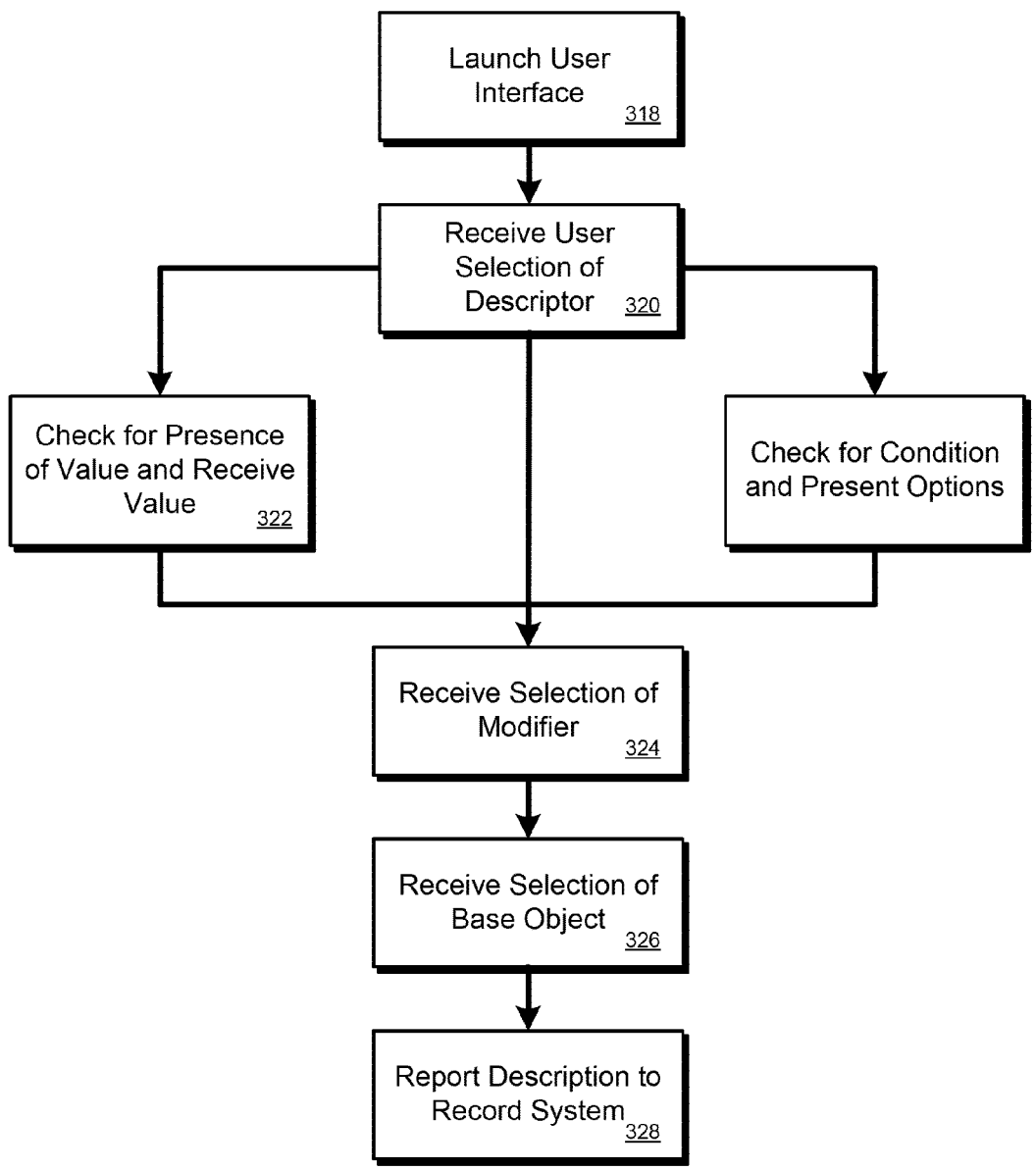

FIGS. 3A and 3B are flow charts of processes for generating healthcare notes from caregiver inputs. In general, FIG. 3A shows actions that occur when a users selects icon on a GUI in an ordered fashion, while FIG. 3B shows a flowchart that permits for options in which a user selects icons.

Referring now to FIG. 3A, the process begins at box 302, where a software application for a particular practice area is instantiated. Such instantiated may occur by a healthcare provider selecting an icon on a computer desktop for the application. The particular practice area may be selected based on where the computer is located (e.g., in an ICU), based on the identity of the provider (which may be determined by fingerprint swipe, login credentials, or similar mechanisms), or based on the most recently-entered information on a computer. For example, a physician may enter information about a particular procedure that was performed on a patient, and then the physician switches to another procedure or another patient, the practice area may stay the same.

Instantiation of the application may cause one or more groups of icons to be displayed on a GUI for the system. For example, the groups may be arranged by category and ordered as shown in FIGS. 1A and 1B above. The groups may represent a variety of parameters, including sizes or volumes of items provided to a patient, the type of worker treating the patient, the disease treated by the caregiver, the type of medical instrument used on the patient, the type of drug given to the patient, and the type of consumables used on the patient (e.g., compression bandage, etc.). The groups may be selected contextually, such as by selecting particular groups to display the a particular practice or specialty area. Also, the groups may be selected by the caregiver providing an initiating input, such as by scanning a bar code near the computer for a particular parameter, or scanning a bar code on a package or instrument that was used with a patient.

At box 304, the process receives a user selection on a descriptor object, which may take the form of a grammatical noun. The description object, in other words, may be in a category of tangible things that the caregiver has used on the patient, such as a stethoscope, a bandage, a syringe, or similar such item. The descriptor object may also represent the caregiver himself or herself. Such a selection may occur by a user pressing their finger or moving an icon on a display of a computer and pressing down on the icon.

At box 306, a user selection on a modifier is received. The modifier may relate to the selected object, and may narrow the scope of the object. For example, the modifier may describe a category of verbs that relate to actions that may be performed with the object. The modifier may also express a procedure performed with the selected object. In addition, the modifier may express a size of the selected object, or a model type of the selected object. For example, if the object is a bandage, the modifier may specify whether is a gauze bandage, an adhesive bandage, an elastic bandage, or another form of bandage.

The modifier may in turn lead to the selection of a further modifier. For example, four columns of selectable icons could be displayed rather than the three shown in FIGS. 1A and 1B, or pop-out selections may be provided for the object or for the modifier. For example, where the modifier is a model number identifier, the extra modifier may specify a size or sub-model number. The extra modifier, in addition to being in a fourth column or row next to the column or row for the initial modifier, and also appear in contextual pop-out menus from the modifier row or column. The user may then slide their finger up or down in the pop-out menu to select a value in the menu, and the pop-up may then disappear, though the selected value may stay displayed until the user finishes selecting one entry for the second modifier category.

At box 308, the process receives a user selection on base object, such as on an image of a human body. The selection here and the prior selections may take the form of the user contacting a touch screen with their fingertip in the first instance, and then sliding it across the screen without lifted in, in a row from one side to the other, and then releasing the finger from the touch screen over an appropriate body part so as to select that body part as the target of a caregiver action performed on the patient.

At box 310, a descriptor ontology is accessed. The ontology may be programmed to produce phrases or sentences that have open portions in them, where the open portions are to be entered based on the icons that the user has selected above. The ontology may be a standard ontology is used for a variety of purposes, or can be a custom ontology that was prepared by or for a particular user.

At box 312, a textual description of a note is built using the ontology. For example, words or phrases that represent the selected object and modifier may be inserted into a phase where blanks existed in the ontology, much like a MAD LIBS interactive children's workbook. The building of the note may also take forms such as using word selection rules that are arranged in a particular order, a hierarchical phrase tree that is traversed to identify appropriate portions to add to a blank phrase in an ontology, or other similar approach.

At box 314, a textual description of an action performed by the caregiver is provided to an EMR system. The textual description may simply be a prose description of the actions that were entered via icons by the caregivers, or can be an appropriate set of descriptors need to populate a patient records, to request reimbursement for particular actions, or other such forms. Also, in particular circumstances, multiple sub-systems may be contacted at this point. For example, an EMR system may receive the description and may append it to the end of a chronological listing of actions that have been performed on a patient. Other uses of the description, by the EMR or another sub-system, may also made.

FIG. 3B shows a process by which a user has multiple options in making selections to build a textual instruction. The process begins at box 319, where the particular user interface is launched. Such a launch may occur by a caregiver logging into a computer, where a preference file for the caregiver could be accessed to determine the form of user interface that the particular caregiver prefers. For example, the caregiver may prefer an interface like those shown above, at least in situation in which such input mechanisms are useful, and icons and actions for generated a description are supported by the system. The launch may also occur by such a user navigating through a system until they reach an action that requires them to generate a textual description of actions they performed. At such an instance, a textual input mechanism may first be shown, and an icon for a graphical input mechanism may be displayed, so that the caregiver may select the icon and be transitioned to an alternative input mechanism if they select the icon.

At box 320, the process receives a user selection of a descriptor. The descriptor may take a variety of forms, and in certain instances may be selected by simply selecting the icon of the descriptor, in which case the process may move on to box 324. However, the descriptor may also take a number of parameters, such as the size or model of a particular medical disposable. Thus, when the user selects the descriptor, the process may be programmed to check whether the selected descriptor defines any parameters, and if it does, a user interface element asking the user to enter the value, such as is shown in FIG. 5A.

The descriptor may also impose certain conditions on the remainder of the input a user may provide. For example, if the descriptor that is initially selected is a body part, the condition may be imposed to limit the display of other icons to actions and materials that may be used to treat the particular body part. The particular options may thus be reduced from an initial set by using various rules for the particular descriptors that a user may select.

At box 324, a user selects a modifier to go with the descriptor. The modifier may be used to define additional information about the descriptor, so as to more definitely define what a textual description of actions performed on a patient. For example, the modifier may identify a treatment provided to a patient, after the descriptor describes a diagnosis for the patient.

At box 326, the process receives a user selection of a base object. Again, the base object in this example, can be a portion of a human body, and a user may select that portion by having an entire image of a human provided to them. Also, where prior selections suggest a particular portion of the body (e.g., by excluding the head or torso from being a likely target, and those portions may be removed form the figure displayed to the caregiver so as to focus the caregiver on the appropriate body parts.

Finally, at box 328, the description is reported to a record keeping system. Such reporting may occur form one application to another in a healthcare information system, or may occur from a plug in to an application. For example, an initial application may prompt users for textual input. The process described here may be implemented as a plug in that intercepts signals regarding user interactions, and transforms such actions into a form that can be used by the application, such as prose text that would otherwise have to be typed in by the caregiver.

In this manner, the listed processes may permit a caregiver to enter extensive data about a process without having to type every character for a description. The caregiver may be shown context-sensitive icons that are readily understandable by a caregiver, even when the caregiver is not fully attentive. Also, unselected icons can change as a user selects icons from other groups, so that the particular icons within a group to be selected in the future are directly responsive to selections that have already been made. Rules may also be imposed so that a user cannot create a description that is not possible (e.g., applying an adhesive bandage to a particular internal organ).

Figures 4, 5:
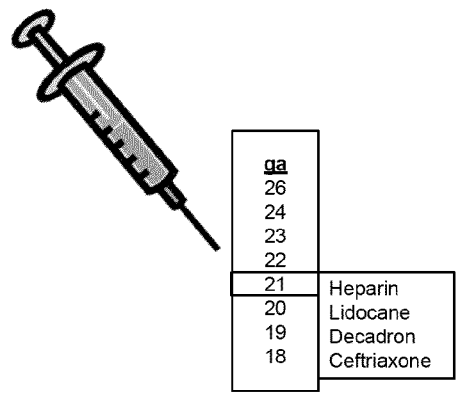
FIG. 4 is an example image for onscreen selections of sub-icons inputs for a healthcare recordkeeping system.
FIG. 5 is an example of a syntax for converting graphical user selections into textual descriptions.

FIG. 4 is an example image for onscreen selections of sub-icon inputs for a healthcare record keeping system. The figure in particular shows an example interface for entering information about provision of a syringe of a drug to a patient. In such an example, the image of the syringe may initially be shown on a touch screen, such as in a modifier column that indicates a treat that was given, and when an object column that was previously selected shows the ailment of the patient for which the shot was given. As the caregiver sweeps his or her finger across the icons and comes to the syringe icon, the box shown to the right of the syringe may pop up and become visible. In this example, the box shows different sizes of syringe. It may be important for a medical record to reflect the size of syringe that was used for various reasons, and it may also affect the amount that the caregiver's employer can be reimbursed for the action. Moreover, identification of the appropriate size of the consumable can assist in operating an automated inventory management system.

In this example, the caregiver has selected a 21 gauge needle by moving his or her finger to the right of the syringe, and then dragging his or her finger downward in the list to 21. Such an action may then cause another pop-up to appear to the right of the first pop-up and aligned with the 21 entry. This second pop-up may show a list of drugs that may be delivered in a particular situation via a 21 gauge needle. Such drugs may include, for example, ceftriaxone, lidocaine, decadron, and heparin, among others. Both lists may be contextual, in that a caregiver may have made a prior selection, such as a selection of a body part, and the sizes and drugs may reflect only those that would normally be given to that body part.

Where a list of parameter values is very long, the caregiver may be provided with a shortened list and an opportunity to scroll through the items in the shortened list. For example, and up arrow and a down arrow may appear adjacent a list and a user may move his or her finger over one of the arrows to scroll. The system may also use multi-touch to permit such manipulation, such as by a user spreading two fingers apart to expand a list of values and pinched the fingers together to contract the list.

Visual indications may be provided with icons that have additional parameters that a caregiver must define. For example, three dots, or an ellipses, may be shown next to icons that require additional input, so that the caregiver can know to expect to be required to provide such additional input as he or she drags across a display. The caregiver may thus slow down when reaching some icons, knowing that he or she cannot easily continue dragging to the next category-based column.

Also, a user's attempt to drag to a next category-based column may be blocked in appropriate circumstances where the user has not entered the appropriate parameter values. For example, an icon may normally drag along with a user's finger as they drag the finger across a screen, so that the user picks up icons while moving, and thereby providing feedback to the user that the icon has been recognized by the system as being selected. Where parameter values need to be entered and they are not, the particular icon can refuse to move along with the user's finger, and the user may thus understand that they need to slide back and see what additional things need to be completed by them.

The pop-up boxes could also appear elsewhere on a display, other than adjacent a particular icon, and could be selected in a different order than that indicated here. For example, a screen could have three category-based columns of icons and a user could drag across all the columns as an initial input. Various boxes may then appear at the bottom of the screen, indicating parameters that a user need to provide for each of the various items that they selected. They may then tap on each parameter in turn and select an appropriate value for it. In building a textual description for the caregiver's action then, the parameters may be inserted as adjectives or adverbs that modify the particular object, e.g., "a 21 gauge heparin syringe."

As another example, where a physician indicates the performance of a laceration repair, the physician may select a laceration and a location of the laceration, and may then select additional modifiers relating the size of suture used, the number of sutures placed, the complexity of repair, and other relevant parameters. As yet another example, where a physician indicates the performance of a physical exam, the physician could start with a location on the body to indicate the area, organ, or system for which information is being provided, and may select modifiers such as the intensity of a murmur, the intensity of abdominal tenderness, and other similar meta data to accompany the main information. Such selections may likewise be constructed into a prose description using semantic rules or other appropriate constructs.

FIG. 5 is an example of syntax for converting graphical user selections into textual descriptions. Such syntaxes may be developed by system designers to match icon entries on a system, and to match understood standards for describing medical actions performed on patients. A system may initially be programmed with a number of such syntaxes, and a customer could acquire (e.g., by download) updated syntaxes over time in a familiar manner, so as to be able to describe new procedures or to comply with regulatory changes. In addition, the rules for syntaxes may also be published, so that customers can easily program their own custom syntaxes.

In the figure, there is shown a syntax for describing the administration of a particular drug to a patient. The first line shows the syntax for a description, where literals in the description are shown outside of brackets and variable are shown inside brackets. The literals are thus "Administered . . . to . . . to treat . . . ." While additional values may be defined, the values for the last modifier are shown here. That modifier indicates what was treated. The first definition below the syntax indicates that the modifier may take three forms: laceration, fracture, and sick—though a full definition would have many other options. The laceration option in turn has a number of variable to define the length of the laceration, and the fracture has defined variables to indicate possible types of fractures. Thus, for example, the description could end with " . . . to treat a greenstick fracture." Each of the three main modifiers in description may be defined separately according to a column that they will take in a graphical user interface. Such assignments may be made simply such as by providing a two-column table, in which each row represents a column in the interface and an ID for the relevant modifier that will appear in that column. For example, the three modifiers here may be assigned names in the syntax and their names may be correlated to particular display columns.

Using this defined syntax, user entries on the interface may be readily interpreted into textual representations. For example, as a user (e.g., a critical care worker) drags across the display, they may be shown a column that includes an icon for a laceration, an icon for a fracture, and an icon for a patient who is sick. If they select one of the icons, and parameters that have been defined with the icon may be displayed as pop-up boxes next to the icon, such as requiring a user to move their finger through a list of laceration sizes if they select the laceration icon in a particular column. The user may then move on to the next column in a similar way, and may select appropriate values for the part of a phrase that is represented by that next column. Such mapping may occur in a relatively simple manner when the interface is a graphical equivalent of the sentence that is to be generated, though the columns in the interface my be rearranged to suit a user's taste—e.g., in subject-verb form or in verb-subject form.

Figure 6:
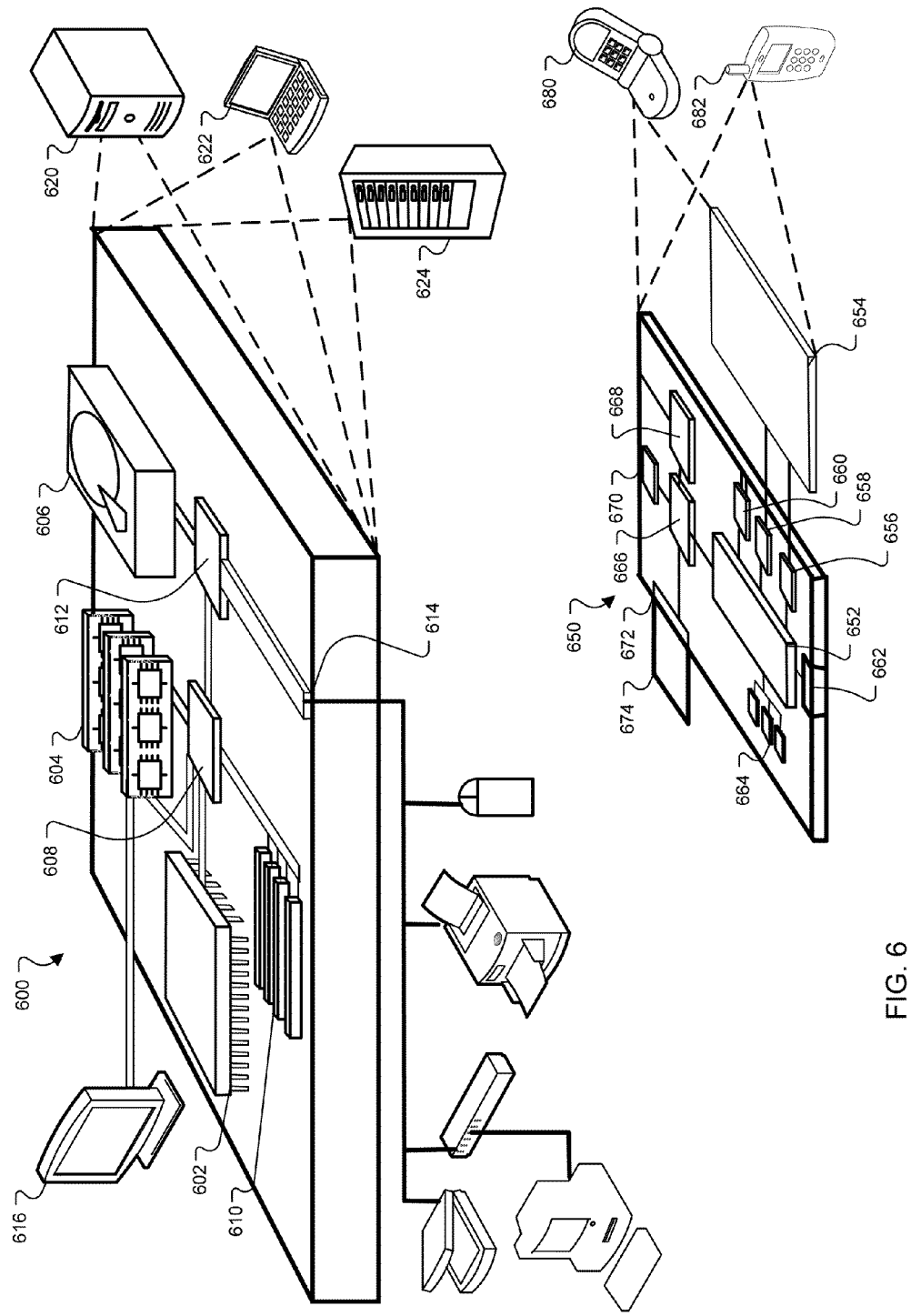
FIG. 6 shows schematic diagrams of a general computer system and a general mobile computing device that may implement the techniques described in this document.

FIG. 6 shows schematic diagrams of a general computer system 500 and a general mobile computing device 550 that may implement the techniques described in this document. Computing device 500 is intended to represent various forms of digital computers, such as laptops, desktops, workstations, personal digital assistants, servers, blade servers, mainframes, and other appropriate computers. Computing device 550 is intended to represent various forms of mobile devices, such as personal digital assistants, cellular telephones, smart phones, and other similar computing devices. The components shown here, their connections and relationships, and their functions, are meant to be exemplary only, and are not meant to limit implementations of the inventions described and/or claimed in this document.

Computing device 500 includes a processor 502, memory 504, a storage device 506, a high-speed interface 508 connecting to memory 504 and high-speed expansion ports 510, and a low speed interface 512 connecting to low speed bus 514 and storage device 506. Each of the components 502, 504, 506, 508, 510, and 512, are interconnected using various busses, and may be mounted on a common motherboard or in other manners as appropriate. The processor 502 can process instructions for execution within the computing device 500, including instructions stored in the memory 504 or on the storage device 506 to display graphical information for a GUI on an external input/output device, such as display 516 coupled to high speed interface 508. In other implementations, multiple processors and/or multiple buses may be used, as appropriate, along with multiple memories and types of memory. Also, multiple computing devices 500 may be connected, with each device providing portions of the necessary operations (e.g., as a server bank, a group of blade servers, or a multi-processor system).

The memory 504 stores information within the computing device 500. In one implementation, the memory 504 is a volatile memory unit or units. In another implementation, the memory 504 is a non-volatile memory unit or units. The memory 504 may also be another form of computer-readable medium, such as a magnetic or optical disk.

The storage device 506 is capable of providing mass storage for the computing device 500. In one implementation, the storage device 506 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 504, the storage device 506, memory on processor 502, or a propagated signal.

The high speed controller 508 manages bandwidth-intensive operations for the computing device 500, while the low speed controller 512 manages lower bandwidth-intensive operations. Such allocation of functions is exemplary only. In one implementation, the high-speed controller 508 is coupled to memory 504, display 516 (e.g., through a graphics processor or accelerator), and to high-speed expansion ports 510, which may accept various expansion cards (not shown). In the implementation, low-speed controller 512 is coupled to storage device 506 and low-speed expansion port 514. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 500 may be implemented in a number of different forms, as shown in the figure. For example, it may be implemented as a standard server 520, or multiple times in a group of such servers. It may also be implemented as part of a rack server system 524. In addition, it may be implemented in a personal computer such as a laptop computer 522. Alternatively, components from computing device 500 may be combined with other components in a mobile device (not shown), such as device 550. Each of such devices may contain one or more of computing device 500, 550, and an entire system may be made up of multiple computing devices 500, 550 communicating with each other.

Computing device 550 includes a processor 552, memory 564, an input/output device such as a display 554, a communication interface 566, and a transceiver 568, among other components. The device 550 may also be provided with a storage device, such as a micro drive or other device, to provide additional storage. Each of the components 550, 552, 564, 554, 566, and 568, are interconnected using various buses, and several of the components may be mounted on a common motherboard or in other manners as appropriate.

The processor 552 can execute instructions within the computing device 550, including instructions stored in the memory 564. The processor may be implemented as a chipset of chips that include separate and multiple analog and digital processors. The processor may provide, for example, for coordination of the other components of the device 550, such as control of user interfaces, applications run by device 550, and wireless communication by device 550.

Processor 552 may communicate with a user through control interface 558 and display interface 556 coupled to a display 554. The display 554 may be, for example, a TFT LCD (Thin-Film-Transistor Liquid Crystal Display) or an OLED (Organic Light Emitting Diode) display, or other appropriate display technology. The display interface 556 may comprise appropriate circuitry for driving the display 554 to present graphical and other information to a user. The control interface 558 may receive commands from a user and convert them for submission to the processor 552. In addition, an external interface 562 may be provide in communication with processor 552, so as to enable near area communication of device 550 with other devices. External interface 562 may provide, for example, for wired communication in some implementations, or for wireless communication in other implementations, and multiple interfaces may also be used.

The memory 564 stores information within the computing device 550. The memory 564 can be implemented as one or more of a computer-readable medium or media, a volatile memory unit or units, or a non-volatile memory unit or units. Expansion memory 574 may also be provided and connected to device 550 through expansion interface 572, which may include, for example, a SIMM (Single In Line Memory Module) card interface. Such expansion memory 574 may provide extra storage space for device 550, or may also store applications or other information for device 550. Specifically, expansion memory 574 may include instructions to carry out or supplement the processes described above, and may include secure information also. Thus, for example, expansion memory 574 may be provide as a security module for device 550, and may be programmed with instructions that permit secure use of device 550. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 564, expansion memory 574, memory on processor 552, or a propagated signal that may be received, for example, over transceiver 568 or external interface 562.

Device 550 may communicate wirelessly through communication interface 566, which may include digital signal processing circuitry where necessary. Communication interface 566 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 568. In addition, short-range communication may occur, such as using a Bluetooth, WiFi, or other such transceiver (not shown). In addition, GPS (Global Positioning System) receiver module 570 may provide additional navigation- and location-related wireless data to device 550, which may be used as appropriate by applications running on device 550.

Device 550 may also communicate audibly using audio codec 560, which may receive spoken information from a user and convert it to usable digital information. Audio codec 560 may likewise generate audible sound for a user, such as through a speaker, e.g., in a handset of device 550. Such sound may include sound from voice telephone calls, may include recorded sound (e.g., voice messages, music files, etc.) and may also include sound generated by applications operating on device 550.

The computing device 550 may be implemented in a number of different forms, as shown in the figure. For example, it may be implemented as a cellular telephone 580. It may also be implemented as part of a smart phone 582, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

A number of embodiments have been described. Nevertheless, it will be understood that various modifications may be made without departing from the spirit and scope of the invention. For example, much of this document has been described with respect to smart phones and similar client devices, but other forms of devices may be employed, including jackets for portable devices where the jackets have been provided with some or all of the functionality just described. For example, a jacket for a smart phone could be provided with a pair of metal plates in the jacket to form a large capacitor which may be used to measure force of a user pressing down on a victim's chest during CPR, and such sensed force may be passed to the smart phone, such as through a physical port on the smart phone or a wireless connection. patient monitoring and reporting may also be addressed.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

What is claimed is:

1. A computer-implemented method for producing healthcare data records from graphical inputs by computer users, the method comprising:

identifying a plurality of user input categories;
displaying on a graphical display, and in a first zone, a plurality of icons that correspond to a first of the user input categories, and receiving in the first zone a first user selection of a first icon of the plurality of icons;
displaying on the graphical display, in a second zone that is spatially separated from the first zone and has an edge that is nearest to the first zone that does not overlap an edge of the first zone that is nearest the second zone, a plurality of icons that correspond to a second of the user input categories, and receiving in the second zone a second user selection of a second icon of the plurality of icons;
displaying on the graphical display one or more icons that correspond to a physical target on which a medical action or observation is performed, and receiving at the one or more icons that correspond to the physical target a third user selection of the physical target; and
applying a syntax to topics of the first, second, and third selections to generate a grammatical description of the medical action or observation using the at least two of the first, second, and third user selections, the syntax being applied to building the grammatical description from multiple separate sub-sentence clauses after at least one of the first, second, and third user selections are received,
wherein one of the first or second user input categories represents an object on which an action is performed, and the other of the first or second input categories represents the action that is performed on the object, and
wherein icons in the second zone are displayed for any selection by the user in the first zone.

2. The method of claim 1, wherein at least two of the first, second, and third user selections are made by a dragging motion of a user dragging their finger or a stylus continuously across a touch screen display on which the icons are shown, without releasing contact with the touch screen until all selections are made.

3. The method of claim 2, wherein the dragging motion moves in a single direction through the first icon, the second icon, and the physical target.

4. The method of claim 2, further comprising cancelling an input operation if the user releases contact with the touch screen display before making all three selections.

5. The method of claim 1, wherein the physical target is selected before the second icon is selected, and the second icon is selected before the first icon is selected, so that a user specifies a physical target for an action before specifying the action.

6. The method of claim 1, further comprising, after receiving the selection of the first icon, changing icons displayed in the second of the user input categories, to provide icons that correspond to the selected icon.

7. The method of claim 6, wherein the changed icons comprise icons of modifiers for a medical procedure or observation selected with the first icon.

8. The method of claim 1, wherein applying a syntax to populate a data record of the action using the at least two of the first, second, and third user selections comprises:
identifying at least an object and an action that correspond to the user inputs; and
constructing a sentence from a template or tree, and adding the object and the action to the template.

9. The method of claim 1, wherein applying a syntax to populate a data record of the action using the at least two of the first, second, and third user selections comprises:
identifying at least two objects and an action that correspond to the user inputs; and
constructing a sentence using a syntactical structure by adding the at least two objects as a grammatical subject and object of the sentence, and the action as a grammatical verb form of the sentence.

10. The method of claim 1, further comprising identifying a patient who corresponds to the user selections, and adding a natural language sentence generated using the syntax.

11. A computer-implemented system for producing healthcare data records from graphical inputs by caregivers, the system comprising:
a display controller to generate data for displaying graphical icons in a plurality of categories, wherein the categories represent a physical target in association with which a medical action is performed, an object that corresponds to a healthcare treatment or action, and a modifier that represents a modification of the object that corresponds to a health care treatment or action, and wherein icons for each of the categories are displayed in separate zones of a graphical display;
an input processor to receive user selections of graphical icons on the graphical display; and
a description builder programmed to apply syntactical rules based on the selected graphical icons to produce a prose of a description for a medical action represented by the selected graphical icons, the prose representing a grammatically complete description that is separate from the displayed categories, wherein the syntactical rules are applied to produce the prose description from multiple separate clauses after at least one user selection is received, and
wherein a first zone of the separate zones of the graphical display has an edge that is nearest to a second zone of the separate zones of the graphical display that does not overlap an edge of the first zone that is nearest the second zone.

12. The system of claim 11, wherein the display controller is programmed to change icons displayed in a second group of displayed icons, in response to a user selection of an icon in a first group of icons.

13. The system of claim 11, wherein the display controller is programmed to arrange the groups of icons visually in three rows or columns, with the physical target in one end row or column, the object that corresponds to a healthcare treatment in the other end row or column, and the modifier in the middle row or column.

14. The system of claim 11, wherein the input processor is programmed to identify a continuous dragging motion across a touch screen display on which the icons are shown, without releasing contact with the touch screen until all selections are made.

15. The system of claim 11, wherein the description builder is programmed to reference a plurality of syntactical rules and to add terms to a sentence based on the user-selected icons.

16. The system of claim 11, wherein the display controller is programmed to change a second group of displayed icons, in one or more columns or rows, in response to a user selection in a first group of displayed icons.

17. The system of claim 11, further comprising an electronic medical record interface to receive the prose for the description, to identify a patient who corresponds to the healthcare treatment or action, and to add the prose description to an electronic medical record for the identified patient.

18. The system of claim 17, wherein the electronic medical record interface is programmed to store the prose description as a sentence in which: (a) the object that corresponds to the healthcare treatment or action is expressed as a grammatical subject; (b) the physical target is expressed as a grammatical object; and (c) the modifier is expressed as a grammatical modifier.

19. The system of claim 17, wherein the electronic medical record interface is programmed to store a syntactical description of the healthcare treatment or action.

20. A computer-implemented system for producing healthcare data records from graphical inputs by caregivers, the system comprising:

a display controller to generate data for displaying graphical icons in a plurality of categories, wherein the categories represent a body part on which an medical action is performed or observed, an object that corresponds to a healthcare treatment or observation, and a modifier that represents a modification of the object that corresponds to a health care treatment or observation, and wherein icons for each of the categories are displayed in separate zones of a graphical display;

an input processor to receive user selections of graphical icons on a graphical display; and means for building a prose description of a medical action represented by the selected graphical icons, the prose description representing a grammatically complete description that is separate from the displayed categories, and the building of the prose description occurs from multiple separate sub-sentence clauses after at least one of the user selections of graphical icons is received, wherein a first zone of the separate zones of the graphical display has an edge that is nearest to a second zone of the separate zones of the graphical display that does not overlap an edge of the first zone that is nearest the second zone.

* * * * *